US011536678B2

(12) United States Patent
Makaram et al.

(10) Patent No.: US 11,536,678 B2
(45) Date of Patent: Dec. 27, 2022

(54) GAS SENSING DEVICE AND METHOD FOR OPERATING A GAS SENSING DEVICE

(71) Applicant: Infineon Technologies AG, Neubiberg (DE)

(72) Inventors: Prashanth Makaram, Berlin (DE); Cecilia Carbonelli, Munich (DE); Caterina Travan, Munich (DE)

(73) Assignee: Infineon Technologies AG, Neubiberg (DE)

(*) Notice: Subject to any disclaimer, the term of this patent is extended or adjusted under 35 U.S.C. 154(b) by 168 days.

(21) Appl. No.: 17/144,948

(22) Filed: Jan. 8, 2021

(65) Prior Publication Data

US 2021/0285907 A1   Sep. 16, 2021

(30) Foreign Application Priority Data

Mar. 11, 2020 (EP) .................................... 20162333

(51) Int. Cl.
*G01N 27/12* (2006.01)
*G06N 3/04* (2006.01)
*G06N 3/08* (2006.01)

(52) U.S. Cl.
CPC ............. *G01N 27/122* (2013.01); *G06N 3/04* (2013.01); *G06N 3/08* (2013.01)

(58) Field of Classification Search
None
See application file for complete search history.

(56) References Cited

U.S. PATENT DOCUMENTS

| 2013/0171733 A1 | 7/2013 | Haick et al. |
| 2015/0308996 A1 | 10/2015 | Kim et al. |

(Continued)

FOREIGN PATENT DOCUMENTS

| CN | 109556731 A | 4/2019 |
| CN | 110426425 A | 11/2019 |
| WO | 0136961 A1 | 5/2001 |

OTHER PUBLICATIONS

Nguyen et al. ("Multi gas sensors using one nanomaterial, temperature gradient, and machine learning algorithms for discrimination of gases and their concentration," Analytica Chimica Acta, vol. 1124, 2020, pp. 85-93, ISSN 0003-2670); (Year: 2020).*

(Continued)

*Primary Examiner* — Roy Y Yi
(74) *Attorney, Agent, or Firm* — Slater Matsil, LLP

(57) ABSTRACT

A gas sensing device includes gas sensors for generating signal samples corresponding to a concentration of a gas; a heat source for heating the gas sensors according to a first temperature profile during recovery phases and according to a second temperature profile during sense phases, a preprocessing processor for preprocessing the received signal samples; a feature extraction processor for extracting feature values from the preprocessed signal samples; a humidity processor for estimating a humidity value of the mixture of gases, including a first trained model based algorithm processor, and wherein the humidity value is based on an output of the first algorithm processor; a gas concentration processor for creating sensing results, wherein the gas concentration processor comprises a second trained model based algorithm processor, wherein the sensing results are based on output values of the second algorithm processor, and wherein the sensing results depend on the humidity value.

20 Claims, 12 Drawing Sheets

(56) References Cited

U.S. PATENT DOCUMENTS

2019/0145929 A1     5/2019   Carbonelli et al.
2020/0271605 A1*    8/2020   Carbonelli ............... G06N 3/08

OTHER PUBLICATIONS

Bekir, Mumyakmaz et al., "A study on the development of a compensation method for humidity effect in QCM sensor responses", Sensors and Actuators B: Chemical, vol. 147, No. 1, Mar. 16, 2010, XP055505450, NL ISSN: 0925-4005, DOI: 10.1016/j.snb.2010.03.019, 6 pages.

Rüffer, Daniel et al., "New Digital Metal-Oxide (MOx) Sensor Platform", Sensors, MDPI, Mar. 31, 2018, Switzerland, 12 pages.

* cited by examiner

GAS SENSING DEVICE AND METHOD FOR OPERATING A GAS SENSING DEVICE

This application claims the benefit of European Patent Application No. 20162333.7, filed on Mar. 11, 2020, which application is hereby incorporated herein by reference.

TECHNICAL FIELD

Embodiments relate to a gas sensing device for sensing one or more gases in a mixture of gases. Further embodiments relate to a method for operating such gas sensing device. More particular, the disclosure deals with the estimation of gas concentrations through the use of chemo-resistive gas sensors.

BACKGROUND

The current disclosure is related to gas sensing technology. Chemo-resistive gas sensors are affected by variation in the environment. Thus, it is important to compensate for environmental changes in-order to accurately identify gases and/or predict their concentrations.

SUMMARY

A gas sensing device for sensing one or more gases in a mixture of gases is provided. The gas sensing device comprises:

one or more chemo-resistive gas sensors, wherein each of the gas sensors is configured for generating signal samples corresponding to a concentration of one of the one or more gases in the mixture of gases, wherein the one or more gas sensors are alternately operated in recovery phases and in sense phases, wherein at least some of the signal samples of each of the gas sensors represent one of the recovery phases and one of the sense phases;

one or more heat sources for heating the gas sensors according to one or more first temperature profiles during the recovery phases and according to one or more second temperature profiles during the sense phases, wherein for each of the gas sensors a maximum temperature of the respective first temperature profile is higher than a maximum temperature of the respective second temperature profile;

a preprocessing processor configured for receiving the signal samples from each of the gas sensors and for preprocessing the received signal samples in order to generate preprocessed signal samples for each of the gas sensors;

a feature extraction processor configured for receiving the preprocessed signal samples and for extracting one or more feature values from the received preprocessed signal samples of each of the gas sensors based on characteristics of the received preprocessed signal samples of the respective gas sensor;

a humidity processor configured for receiving a first group of the feature values and for estimating a humidity value of the mixture of gases, wherein the humidity processor comprises a first trained model based algorithm processor and a first trained model for the first trained model based algorithm processor, wherein the first group of feature values is fed to inputs of the first trained model based algorithm processor, and wherein the humidity value is based on an output of the first machine learning algorithm processor;

a gas concentration processor configured for receiving a second group of the feature values and the humidity value, and for creating for each of the gas sensors sensing results, wherein the gas concentration processor comprises a second trained model based algorithm and a second trained model for the second trained model based algorithm processor, wherein the second group of feature values is fed to inputs of the second trained model based algorithm processor, wherein the sensing results are based on output values at one or more outputs of the second machine learning algorithm processor, and wherein the sensing results depend on the humidity value.

The one or more chemo-resistive gas sensors may be graphene gas sensors or reduced graphene gas sensors, where the base material is functionalized with specific chemicals, e.g. with platinum (Pt), or manganese dioxide (MnO2), so that each of the gas sensors is sensitive for a specific gas, e.g. for nitrogen dioxide (NO2), ozone (O3) or carbon monoxide (CO). In doing so, the interaction between graphene sheets and absorbed gas analytes influences the electronic structure of the material depending on the mixture of gases, resulting in altered charge carrier concentration and changed electrical conductance.

In case of multi-gas sensing a multi-gas sensor array comprising a plurality of chemo-resistive gas sensors having dissimilar selectivity may be used. Due to the different sensitivity towards various gas molecules, resistances of the gas sensors change in disparate patterns, making it possible to analyze complicated gas mixtures with one single sensor array.

A signal sample is a sequence consisting of time-discrete signal values, wherein the signal values are output by one of the gas sensors.

Each of the gas sensors may be heated by one or more heat sources. The heat sources may be electrically powered resistive heating elements or radiators emitting light, in particular with ultra violet light. Each of the one or more heat sources is controlled according to a first temperature profile during the recovery phases and according to a second temperature profile during the sense phases, wherein a maximum temperature of the first temperature profile is higher than a maximum temperature of the second temperature profile.

For example, the temperature of the one or more heating elements may be pulsed between a first temperature during the recovery phases of the gas sensors and a second temperature during the sense phases of the gas sensors, wherein the first temperature is higher than the second temperature. The first temperature may be, for example, set to a value between 150° C. and 300° C., whereas the second temperature may be, for example, set to a value between 50° C. and 200° C.

The temperature modulation could be the same for all sensors.

In order to improve repeatability and stability of the sensing results, at least some of the signal samples of each of the gas sensors represent at least one of the recovery phases and at least one of the sense phases.

The term processor refers to an electronic device configured for specific task. A processor may comprise hardware or a combination of hardware and software. Different processors may share hardware components and/or software components.

The pre-processing processor is configured for suppressing and/or compensating of artifacts in the signal samples and/or noise in the signal samples and/or invalid signal samples due to malfunctioning gas sensors and/or errors in the signal samples due to drifts of the gas sensors in order to produce more reliable filtered signal samples.

The information extraction processor is configured for receiving the preprocessed signal samples and for extracting one or more feature values from the received preprocessed signal samples of each of the gas sensors based on characteristics of the received preprocessed signal samples of the respective gas sensor. The features may be based on dynamic characteristics of the signal samples. To this end, the pulsed nature of the responses of the gas sensors is leveraged and characteristics are extracted which rely on the dynamic evolution of the gas sensors.

A trained model based algorithm processor is a processor which is capable of machine learning. The machine learning is done in a preoperational training phase in which trained models are developed by comparing actual output values of the trained model based algorithm stage with desired output values of the trained model based algorithm stage for defined inputs of the trained model based algorithm stage. The trained models have a predefined structure, wherein a parametrization of the predefined structure is done during the training phase. The trained models comprise the learned content after the training phase is finished. In an operational phase for producing processing results one or more of the trained models from the training phase are used to process their input data.

In the training phase the plurality of trained models can be established and afterwards stored at the gas sensing device. The trained models may differ in the structures and/or the parameters. During the operation phase the most appropriate trained model may be selected depending on the on the specific use-case.

The humidity processor is configured for receiving a first group of the feature values as input data and for estimating a humidity value of the mixture of gases as its processing result, wherein the humidity processor comprises a first trained model based algorithm processor and a first trained model for the first trained model based algorithm processor, wherein the first group of feature values is fed to inputs of the first trained model based algorithm processor, and wherein the humidity value is based on an output of the first machine learning algorithm processor. The working principle of the humidity processor is based on the idea that dynamic characteristics of the signal samples from the chemo-resistive gas sensors are directly influenced by the ambient humidity. Although the direct influence of the humidity on the signal samples is per se not known in terms of quantity and quality, the use of the first trained model based algorithm processor allows exploiting the influence for estimating the humidity value so that a dedicated humidity sensor is not necessary in order to create the humidity value.

The gas concentration processor is configured for receiving a second group of the feature values and the humidity value, and for creating for each of the gas sensors sensing results, wherein the gas concentration processor comprises a second trained model based algorithm and a second trained model for the second trained model based algorithm processor, wherein the second group of feature values is fed to inputs of the second trained model based algorithm processor, wherein the sensing results are based on output values at an output of the second machine learning algorithm processor, and wherein the sensing results depend on the humidity value.

The second group of the feature values may comprise the same feature values or different feature values compared to the first group of feature values.

The gas concentration processor provides a decision on the classification of gas concentrations detected by the gas sensors or a continuous measurement of gas concentrations detected by the gas sensors. In the first case a second trained model, which is trained as a classification algorithm, is used and the sensing results are alphanumeric terms such as "high" or "low". In particular, the terms of an air quality index system may be used for outputting the sensing results. In the latter case a second trained model, which is trained as a regression algorithm, is used and the sensing results are physical quantities such as "4% by volume". The gas concentration processor takes the humidity value provided by the humidity processor into account so that an influence of the ambient humidity on the sensing results is minimized or even eliminated.

The gas sensing device according to the disclosure addresses the intrinsic instability of chemo-resistive gas sensors. It uses robust algorithms and detection mechanisms which can cope with calibration inaccuracies, drifts and other similar effects reliably and over a wide operating range.

The proposed gas sensing device provides an end to end solution for multi-gas adsorption sensors which is versatile, widely-applicable to multiple applications and uses cases (outdoor, indoor, health check, etc.) and can be embedded in a smart portable device. Specifically, an algorithm is used that works on continuous sensor readings, makes use of the transient information in the sensor responses and exhibits low complexity and limited memory requirements.

The gas sensing device can reflect real world scenarios, where, for example, gas mixtures are present which are causing cross-sensitivities in the sensor responses, and where the ambient humidity varies. Moreover, the gas sensing device only takes a short time for reaching a stable response level.

Due to the fact that the dedicated humidity sensor is not necessary, the material costs of the gas sensing device are low and it uses concrete mechanisms which are robust and economic enough to be embedded into mass-produced consumer electronic products (like a mobile phone), while delivering good continuous prediction performance in complicated real world scenarios, and as such have to deal with challenges related to the availability of a limited and noisy sets of data, imperfect initial calibration, gas mixtures with varying concentrations of analytes, modelling errors, etc.

In particular, the gas sensing device may be used for air quality monitoring.

The proposed gas sensing device comprises a technique based solely on using the right calibration and implementation of algorithm without using an added sensor component. By extracting the correct features of the gas sensors response (no humidity sensors), it is possible to predict and compensate variations in ambient humidity conditions.

The benefit of this technique is:
reduced long term drift.
improved accuracy of the prediction of gases.
improved classification of gases.
as an added feature, humidity values may be provided without a humidity sensor.

With this technique, there is no need for additional humidity sensors, which leads to:
reduced BOM cost
reduced ASIC complexity and power consumption requirements
no additional R&D effort needed in-house to develop/integrate a humidity sensor
reduced chip size (no space needed for humidity sensor)

According to embodiments of the disclosure the preprocessing processor is configured for executing a baseline calibration algorithm for the signal samples received from the gas sensors. Baseline manipulation is the transformation of a signal sample of one of the gas sensors into a relative resistance change with respect to sensor response to a reference analyte, wherein such sensor response is called a baseline. Synthetic air is a very common baseline as it is easily applicable and realistic in a real world scenario. The purpose of a baseline is to potentially create a more stable and reproducible sensing result by removing some of the drift caused by long term gas exposure and ageing of the sensor. As shown in Equation (1), subtracting the sensor response by its baseline R0 removes additive drift while division removes multiplicative drift. Using both operations combined results in the relative resistance change $\Delta R/R_0$:

$$\Delta R/R_0 = (R-R_0)/R_0 \quad (1)$$

According to embodiments of the disclosure the preprocessing processor is configured for executing a filtering algorithm for the signal samples received from the gas sensors. The filtering algorithm may, for example, be implemented as a high pass filter or a noise filter. Such features further improve the accuracy of the sensing results.

According to embodiments of the disclosure the preprocessing processor is configured for executing a sense phase extraction algorithm for the signal samples received from the gas sensors. These features allow determined whether a specific value of one of the signal samples is generated during one of the recovery phases or during one of the sense phases, which improves the quality of the extraction of the feature values so that the accuracy of the humidity value as well as of the sensing results is improved.

According to embodiments of the disclosure the feature extraction processor is configured for extracting from the received preprocessed signal samples a normalized sensor sensitivity $\Delta R/R_0$ as one of the feature values for each of the gas sensors. The normalized sensor sensitivity $\Delta R/R_0$ may be calculated according to Equation (1).

Using the normalized sensor sensitivities $\Delta R/R_0$ as feature values improves the accuracy of the sensing result.

According to embodiments of the disclosure the feature extraction processor is configured for extracting from the received preprocessed signal samples a slope R'(t) of one of the preprocessed signal samples as one of the feature values for each of the gas sensors. The slope R'(t) or derivative may be calculated according to Equation (2):

$$R'(t)=\Delta R(t)/\Delta t \quad (2)$$

Using the slopes R'(t) as feature values improves the accuracy of the sensing result.

According to embodiments of the disclosure the feature extraction processor is configured for extracting from the preprocessed signal samples received from the gas sensors a ratio r between an average value $\widehat{R_{T2}}$ of one of the preprocessed signal samples during the sense phase of the one of the preprocessed signal samples and an average value $\widehat{R_{T1}}$ of the one of the preprocessed signal samples during the recovery phase of the one of the preprocessed signal samples as one of the feature values for each of the gas sensors. The ratio r may be calculated according to Equation (3):

$$d = \widehat{R_{T1}} - \widehat{R_{T2}} \quad (3)$$

Using the ratio r as feature values improves the accuracy of the sensing result.

According to embodiments of the disclosure the feature extraction processor is configured for extracting from the preprocessed signal samples received from the gas sensors a difference d between an average value $\widehat{R_{T2}}$ of one of the preprocessed signal samples during the sense phase of the one of the preprocessed signal samples and an average value $\widehat{R_{T1}}$ of the one of the preprocessed signal samples during the recovery phase of the one of the preprocessed signal samples as one of the feature values for each of the gas sensors. The difference d may be calculated according to Equation (4):

$$d = \widehat{R_{T1}} - \widehat{R_{T2}} \quad (4)$$

Using the differences d as feature values improves the accuracy of the sensing result.

According to embodiments of the disclosure the first trained model based algorithm processor is implemented as a first artificial neural network.

According to embodiments of the disclosure the second trained model based algorithm processor is implemented as a second artificial neural network.

An artificial neural network is a parameterized statistic model, in which a number of logistic regressions are combined non-linearly. Such systems "learn" to perform tasks by considering examples, generally without being programmed with any task-specific rules. A neural network is based on a collection of connected nodes called artificial neurons. Each connection can transmit a signal from one artificial neuron to another. An artificial neuron that receives a signal can process it and then signal additional artificial neurons connected to it. A model predefines the structure of the nodes or the hyper-parameters of a neural network and the parameters of the connections are found by training the neural network. Structure and the corresponding parameters form a trained model for the respective neural network.

According to embodiments of the disclosure the humidity value is fed to one of the inputs of the second trained model based algorithm processor in order to make the sensing results dependent on the humidity value. By these features the influence of the ambient humidity on the sensing results is learnt automatically by the second trained model based algorithm processor during the training phase. Furthermore, the influence of ambient humidity on the sensing results is compensated automatically during the operational phase.

According to embodiments of the disclosure the gas sensing device comprises a temperature processor configured for receiving a third group of the feature values and for estimating a temperature value of the mixture of gases, wherein the temperature processor comprises a third trained model based algorithm processor and a third trained model for the third trained model based algorithm processor, wherein the third group of feature values is fed to inputs of the third trained model based algorithm processor, and wherein the temperature value is based on an output of the third machine learning algorithm processor;

wherein the gas concentration processor is configured for receiving the temperature value, and wherein the sensing results are based on the temperature value.

The working principle of the temperature processor is based on the idea that dynamic characteristics of the signal samples from the chemo-resistive gas sensors are directly influenced by the ambient temperature. Although the direct influence of the temperature on the signal samples is per se not known in terms of quantity and quality, the use of the third trained model based algorithm processor allows exploiting the influence for estimating the temperature value so that a dedicated temperature sensor is not necessary in order to create the temperature value.

According to embodiments of the disclosure the third trained model based algorithm processor is implemented as a third artificial neural network.

According to embodiments of the disclosure the temperature value is fed to one of the inputs of the second trained model based algorithm processor in order to make the sensing results dependent on the temperature value. By these features the influence of the ambient temperature on the sensing results is learnt automatically by the second trained model based algorithm processor during the training phase. Furthermore, the influence of ambient temperature on the sensing results is compensated automatically during the operational phase.

According to embodiments of the disclosure the gas concentration processor comprises a correction processor for correcting the output values of the second machine learning algorithm processor, wherein the humidity value is fed to the correction processor, wherein the correction processor is configured for correcting the output values of the second machine learning algorithm processor depending on the humidity value in order to make the sensing results dependent on the humidity value. In cases, in which the influence of the ambient humidity on the sensing result is known, a high accuracy of the sensing results may be achieved by using these features.

According to embodiments of the disclosure the gas concentration processor comprises a correction processor for correcting the output values of the second machine learning algorithm processor, wherein the temperature value is fed to the correction processor, wherein the correction processor is configured for correcting the output values of the second machine learning algorithm processor depending on the temperature value in order to make the sensing results dependent on the temperature value. In cases, in which the influence of the ambient temperature on the sensing result is known, a high accuracy of the sensing results may be achieved by using these features.

According to embodiments of the disclosure the correction processor comprises on or more lookup tables for correcting the output values of the second machine learning algorithm processor. By these features a high accuracy of the sensing results may be achieved.

According to embodiments of the disclosure the gas sensing device comprises an output unit configured for outputting the sensing results and/or the humidity value.

According to embodiments of the disclosure the gas sensing device comprises an output unit configured for outputting the temperature value.

By these features the humidity value and/or the temperature value may be outputted so that the user is informed about the ambient humidity and/or the ambient temperature around the gas sensing device. The output unit may be a graphical user interface.

In a further aspect a method for operating a gas sensing device for sensing one or more gases in a mixture of gases is disclosed, wherein the gas sensing device comprises one or more chemo-resistive gas sensors. The method comprises the steps of:

using each of the gas sensors for generating signal samples corresponding to a concentration of one of the one or more gases in the mixture of gases, wherein the one or more gas sensors are alternately operated in recovery phases and in sense phases, wherein At least some of the signal samples of each of the gas sensors represent one of the recovery phases and one of the sense phases;

using one or more heat sources for heating the gas sensors according to one or more first temperature profiles during the recovery phases and according to one or more second temperature profiles during the sense phases, wherein for each of the gas sensors a maximum temperature of the respective first temperature profile is higher than a maximum temperature of the respective second temperature profile;

using a preprocessing processor for receiving the signal samples from each of the gas sensors and for preprocessing the received signal samples in order to generate preprocessed signal samples for each of the gas sensors;

using a feature extraction processor for receiving the preprocessed signal samples and for extracting one or more feature values from the received preprocessed signal samples of each of the gas sensors based on characteristics of the received preprocessed signal samples of the respective gas sensor;

using a humidity processor for receiving a first group of the feature values and for estimating a humidity value of the mixture of gases, wherein the humidity processor comprises a first trained model based algorithm processor and a first trained model for the first trained model based algorithm processor, wherein the first group of feature values is fed to inputs of the first trained model based algorithm processor, and wherein the humidity value is based on an output of the first machine learning algorithm processor;

using a gas concentration processor for receiving a second group of the feature values and the humidity value, and for creating for each of the gas sensors sensing results, wherein the gas concentration processor comprises a second trained model based algorithm processor and a second trained model for the second trained model based algorithm processor, wherein the second group of feature values is fed to inputs of the second trained model based algorithm processor, wherein the sensing results are based on output values at one or more outputs of the second machine learning algorithm processor, and wherein the sensing results depend on the humidity value.

BRIEF DESCRIPTION OF THE DRAWINGS

Embodiments of the present invention are described herein making reference to the appended drawings.

Figure 1:
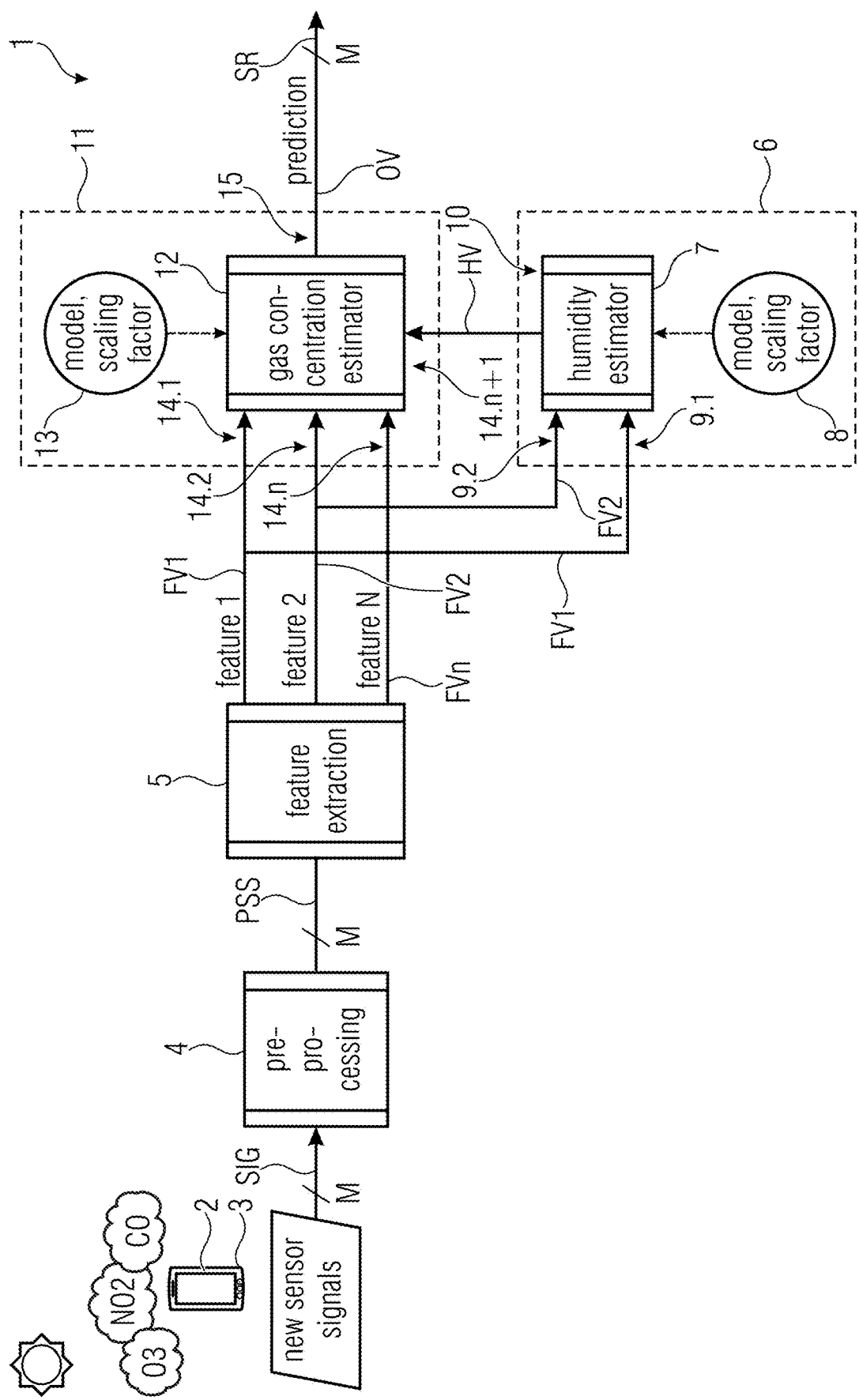
FIG. 1 shows a schematic view of a first exemplary embodiment of a gas sensing device according to the disclosure, which comprises three chemo-resistive gas sensors.

Equal or equivalent elements or elements with equal or equivalent functionality are denoted in the following description by equal or equivalent reference numerals.

DETAILED DESCRIPTION OF ILLUSTRATIVE EMBODIMENTS

In the following description, a plurality of details is set forth to provide a more thorough explanation of embodiments of the present invention. However, it will be apparent to those skilled in the art that embodiments of the present invention may be practiced without these specific details. In other instances, well-known structures and devices are shown in block diagram form rather than in detail in order to avoid obscuring embodiments of the present invention. In addition, features of the different embodiments described hereinafter may be combined with each other, unless specifically noted otherwise.

FIG. 1 shows a schematic view of a first exemplary embodiment of a gas sensing device 1 according to the disclosure, which comprises three chemo-resistive gas sensors 2.

The gas sensing device 1 for sensing one or more gases in a mixture of gases; the gas sensing device 1 comprises:

one or more chemo-resistive gas sensors 2, wherein each of the gas sensors 2 is configured for generating signal samples SIG corresponding to a concentration of one of the one or more gases in the mixture of gases, wherein the one or more gas sensors 2 are alternately operated in recovery phases RP and in sense phases SP, wherein at least some of the signal samples SIG of each of the gas sensors 2 represent one of the recovery phases RP and one of the sense phases SP;

one or more heat sources 3 for heating the gas sensors 2 according to one or more first temperature profiles FTP during the recovery phases RP and according to one or more second temperature profiles STP during the sense phases SP, wherein for each of the gas sensors 2 a maximum temperature of the respective first temperature profile FTP is higher than a maximum temperature of the respective second temperature profile STP;

a preprocessing processor 4 configured for receiving the signal samples SIG from each of the gas sensors 2 and for preprocessing the received signal samples SIG in order to generate preprocessed signal samples PSS for each of the gas sensors 2;

a feature extraction processor 5 configured for receiving the preprocessed signal samples PSS and for extracting one or more feature values FV from the received preprocessed signal samples PSS of each of the gas sensors 2 based on characteristics of the received preprocessed signal samples PSS of the respective gas sensor 2;

a humidity processor 6 configured for receiving a first group of the feature values FV and for estimating a humidity value HV of the mixture of gases, wherein the humidity processor 6 comprises a first trained model based algorithm processor 7 and a first trained model 8 for the first trained model based algorithm processor 7, wherein the first group of feature values FV is fed to inputs 9 of the first trained model based algorithm processor 8, and wherein the humidity value HV is based on an output 10 of the first machine learning algorithm processor 7;

a gas concentration processor 11 configured for receiving a second group of the feature values FV and the humidity value HV, and for creating for each of the gas sensors 2 sensing results SR, wherein the gas concentration processor 11 comprises a second trained model based algorithm processor 12 and a second trained model 13 for the second trained model based algorithm processor 12, wherein the second group of feature values FV is fed to inputs 14 of the second trained model based algorithm processor 12, wherein the sensing results SR are based on output values OV at one or more outputs 15 of the second machine learning algorithm processor 12, and wherein the sensing results SR depend on the humidity value HV.

According to embodiments of the disclosure the preprocessing processor 4 is configured for executing a baseline calibration algorithm for the signal samples SIG received from the gas sensors 2.

According to embodiments of the disclosure the preprocessing processor 4 is configured for executing a filtering algorithm for the signal samples SIG received from the gas sensors 2.

According to embodiments of the disclosure the preprocessing processor 4 is configured for executing a sense phase extraction algorithm for the signal samples SIG received from the gas sensors 2.

According to embodiments of the disclosure the feature extraction processor 5 is configured for extracting from the received preprocessed signal samples PSS a normalized sensor sensitivity as one of the feature values FV for each of the gas sensors 2.

According to embodiments of the disclosure the feature extraction processor 5 is configured for extracting from the received preprocessed signal samples PSS a slope of one of the preprocessed signal samples PSS as one of the feature values FV for each of the gas sensors 2.

According to embodiments of the disclosure the feature extraction processor 5 is configured for extracting from the preprocessed signal samples PSS received from the gas sensors 2 a ratio between an average value of one of the preprocessed signal samples PSS during the sense phase SP of the one of the preprocessed signal samples PSS and an average value of the one of the preprocessed signal samples PSS during the recovery phase of the one of the preprocessed signal samples PSS as one of the feature values FV for each of the gas sensors 2.

According to embodiments of the disclosure the feature extraction processor 5 is configured for extracting from the preprocessed signal samples PSS received from the gas sensors 2 a difference between an average value of one of the preprocessed signal samples PSS during the sense phase of the one of the preprocessed signal samples PSS and an average value of the one of the preprocessed signal samples PSS during the recovery phase of the one of the preprocessed signal samples PSS as one of the feature values FV for each of the gas sensors 2.

According to embodiments of the disclosure the humidity value HV is fed to one of the inputs 14 of the second trained model based algorithm processor 12 in order to make the sensing results SR dependent on the humidity value HV.

In a further aspect a method for operating a gas sensing device 1 for sensing one or more gases in a mixture of gases is disclosed, wherein the gas sensing device 1 comprises one or more chemo-resistive gas sensors 2. The method comprises the steps of:

using each of the gas sensors 2 for generating signal samples SIG corresponding to a concentration of one of the one or more gases in the mixture of gases, wherein the one or more gas sensors 2 are alternately operated in recovery phases RP and in sense phases SP, wherein at least some of the signal samples SIG of each of the gas sensors 2 represent one of the recovery phases RP and one of the sense phases SP;

using one or more heat sources 3 for heating the gas sensors 2 according to one or more first temperature profiles FIT during the recovery phases RP and according to one or more second temperature profiles STP during the sense phases SP, wherein for each of the gas sensors 2 a maximum temperature of the respective first temperature profile FTP is higher than a maximum temperature of the respective second temperature profile STP;

using a preprocessing processor 4 for receiving the signal samples SIG from each of the gas sensors 2 and for preprocessing the received signal samples SIG in order to generate preprocessed signal samples PSS for each of the gas sensors 2;

using a feature extraction processor 5 for receiving the preprocessed signal samples PSS and for extracting one or more feature values FV from the received preprocessed signal samples PSS of each of the gas sensors 2 based on characteristics of the received preprocessed signal samples PSS of the respective gas sensor 2;

using a humidity processor 6 for receiving a first group of the feature values FV and for estimating a humidity value HV of the mixture of gases, wherein the humidity processor 6 comprises a first trained model based algorithm processor 7 and a first trained model 8 for the first trained model based algorithm processor 7, wherein the first group of feature values FV is fed to inputs 9 of the first trained model based algorithm processor 7, and wherein the humidity value HV is based on an output 10 of the first machine learning algorithm processor 7;

using a gas concentration processor 11 for receiving a second group of the feature values FV and the humidity value HV, and for creating for each of the gas sensors 2 sensing results SR, wherein the gas concentration processor 11 comprises a second trained model based algorithm processor 12 and a second trained model 13 for the second trained model based algorithm processor 12, wherein the second group of feature values FV is fed to inputs 14 of the second trained model based algorithm processor 12, wherein the sensing results SR are based on output values OV at one or more outputs 15 of the second machine learning algorithm processor 12, and wherein the sensing results SR depend on the humidity value HV.

The exemplary gas sensing device 1 shown in FIG. 1 comprises three chemo-resistive gas sensors 2, wherein one of the chemo-resistive gas sensors 2 is configured for sensing of O3, one of the chemo-resistive gas sensors 2 is configured for sensing of NO2, and one of the cable-resistive gas sensors 2 is configured for sensing of CO. Each of the chemo-resistive gas sensors 2 generates signal samples SIG, which are forwarded to the preprocessing processor 4 so that M=3 signal samples SIG are forwarded parallelly. The preprocessing processor 4 preprocesses the signal samples SIG of each of the chemo-resistive gas sensors 2 so that for each of the chemo-resistive gas sensors 2 preprocessed signal samples PSS are generated. The preprocessed signal samples PSS for each of the chemo-resistive gas sensors 2 are fed to the feature extraction processor 5 so that M=3 preprocessed signal samples PSS are forwarded parallelly.

The feature extraction processor 5 extracts N-feature values FV from the preprocessed signal samples PSS for each of the chemo-resistive gas sensor 2. For simplicity only the feature values FV1 to FVn originating from the first chemo-resistive gas sensor 2 are shown in FIG. 1.

In the example of FIG. 1 the feature value FV1 originating from the first of the chemo-resistive gas sensors 2 is fed to input 9.1 of the first trained model based algorithm processor 7. Further, the feature value FV2 originating from the first of the chemo-resistive gas sensors 2 is fed to input 9.2 of the first trained model based algorithm processor 7. The feature values FV1 and FV2 originating from the second chemo-assistive gas sensor 2 and the third chemo-assistive gas sensor 2 are parallelly fed to further inputs (not shown) of the first trained model based algorithm processor 7.

Further, the feature value FV1 originating from the first of the chemo-resistive gas sensors 2 is fed to input 14.1 of the second trained model based algorithm processor 12, the feature value FV2 originating from the first of the chemo-resistive gas sensors 2 is fed to input 14.2 of the second trained model based algorithm processor 12 and so on. The feature value FVn originating from the first of the chemo-resistive gas sensors 2 is fed to input 14.n of the second trained model based algorithm processor 12, The feature values FV1 to FVn originating from the second chemo-assistive gas sensor 2 and the third chemo-assistive gas sensor 2 are parallelly fed to further inputs (not shown) of the second trained model based algorithm processor 12.

Moreover, the humidity value HV from the output 10 of the first trained model based algorithm processor 7 is fed to input 14.n+1 of the second trained model based algorithm processor 12. In FIG. 1, the output values OV at the outputs 15 of the second trained model based algorithm processor 12 are equal to the sensing results SR for each of the chemo-resistive gas sensors 2.

FIG. 1 shows the general signal processing flow during inference from feature identification to predictions. Here the raw signals from the M sensors are sampled and filtered and specific features are extracted. Those features that are particularly helpful to extract the humidity information are sent to the humidity estimation block. Such a block could be supervised classifier based on Maximum A-posteriori (MAP) criterion where it is assumed that the likelihood function, that is, the conditional probability $$P([F1,F2]|RHi) \approx 1/(2\pi)n/2|\Sigma RHi|^{1/2} \exp[-\frac{1}{2}(F-\mu RHi)T\Sigma RHi-1(F-\mu RHi)] \quad (5)$$

of the observed feature vector F=[F1, F2] to the given humidity class value RHi, fulfills a unimodal Gaussian density distribution whose covariance matrix ΣRHi and mean vector μRHi have to be determined in the calibration phase and are part of the model deployed later on the target architecture.

The humidity value in the inference (test) phase is then obtained as:

$$RHp = i(P([F1,F2]|RHi)) \quad (6).$$

Other approaches to predict the humidity are possible, for example a non-parametric method such a small fully connected Neural Network with just few nodes and one hidden layer, as depicted in FIG. 6b where some features are shared among the estimator blocks (Feature 1) and some are exclusively used by only one of them (Feature 2, 3, . . . N).

Specifically, the humidity estimates can be obtained as:

$$RH = [W*[F1,F2] + b] \quad (7)$$

where (W, b) are the weights and offsets of the single hidden layer to be optimized with a backpropagation algorithm (and then deployed in the inference phase), σ is the activation functions, and [F1, F2] is the concatenation of the input features.

For the gas concentration estimates $\tilde{C}$ we knew more hidden layers. In case of a feedforward neural network, the final output can be expressed as:

$$C = \sigma[WN[\ldots[[W1*[\tilde{R}H, F1, F2, \ldots, FN] + b1] \ldots] + bN] \quad (8)$$

where $[\tilde{R}H, F1, F2, \ldots, FN] + b1] \ldots$ ] is the concatenation of the estimated humidity $\tilde{R}H$ and the remaining input features [F1, F2, ..., FN] and (Wi, bi) are the weights and the offset of the generic hidden layer 1.

Figure 3:
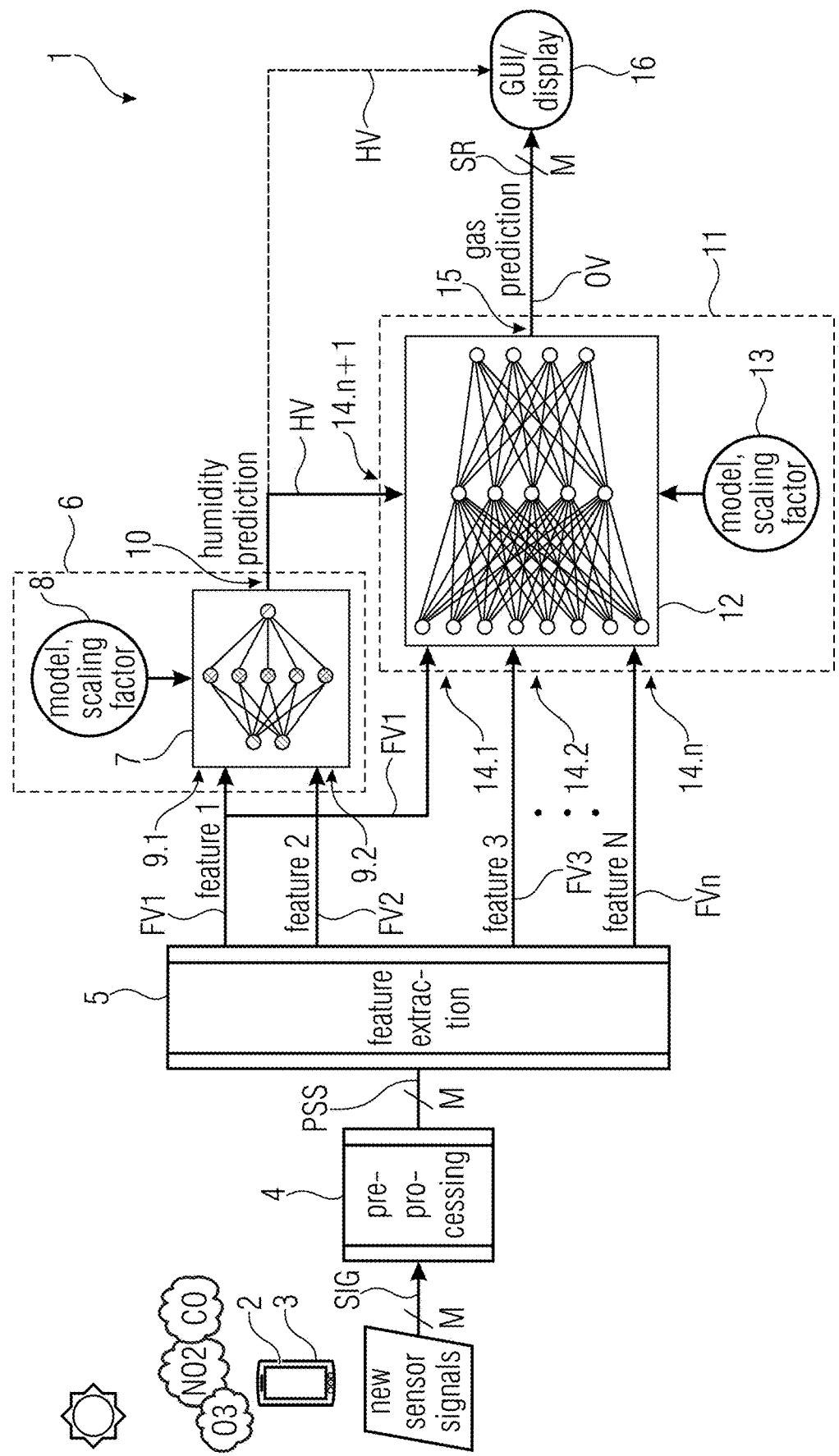
FIG. 3 shows a schematic view of a second exemplary embodiment of a gas sensing device according to the disclosure.

As a summary: FIG. 3 illustrates a deployment of the model with neural networks of different depths.

Figure 2:
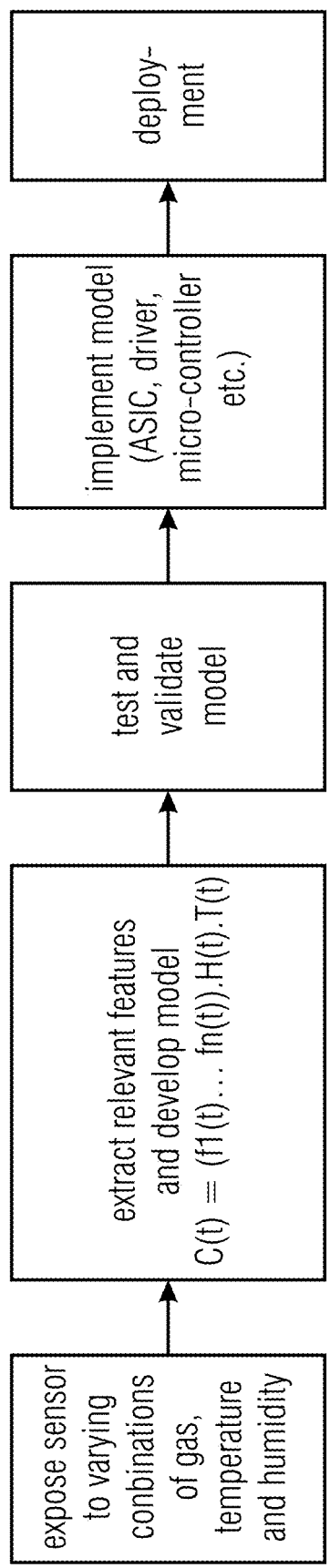
FIG. 2 shows a schematic flow chart describing the development and the implementation of the trained models and the trained model based algorithm processors described herein.

FIG. 2 shows a schematic flow chart describing the development and the implementation of the trained models 8, 13, 19 and the trained model based algorithm processors 7, 12, 18 described herein.

As depicted in FIG. 2, a preliminary calibration phase is first carried out to extract the relevant feature values FV out of the sensors signal samples SIG. These feature values FV are then combined to develop one simpler first trained model 8 that ac-counts for humidity and a second trained model 13 that accounts for gas concentrations.

The trained models 8 and 13 are then deployed together with the necessary inference steps on the target architecture and used to predict concentrations SR (and if needed humidity values HV) in real time. The flow chart describes the model development and implementation, wherein C(t) denotes the concentration as a function of time, f1(t) ... fn(t) denotes features 1 to n as a function of time, H(t) denotes humidity as a function of time and T(t) denotes temperature as a function of time.

It has to be noted that one global model could be trained with both humidity and gas concentrations as target outputs; however, this has shown poorer performance in terms of gas estimation and a higher complexity in terms of number of parameters for equivalent accuracy particularly when a separate humidity estimate needs to be provided to the user. Therefore, a two-stage approach with separate humidity and gas estimation shall be preferred as depicted in FIG. 1.

FIG. 3 shows a schematic view of a second exemplary embodiment of a gas sensing device 1 according to the disclosure. The second embodiment is based on the first embodiment so that in the following only the differences are discussed.

According to embodiments of the disclosure the first trained model based algorithm processor 6 is implemented as a first artificial neural network.

According to embodiments of the disclosure the second trained model based algorithm processor 12 is implemented as a second artificial neural network.

According to embodiments of the disclosure the gas sensing device 1 comprises an output unit 16 configured for outputting the sensing results SR and/or the humidity value HV.

As a summary: FIG. 3 illustrates a deployment of the overall model with two neural networks of different depths.

Figure 4:
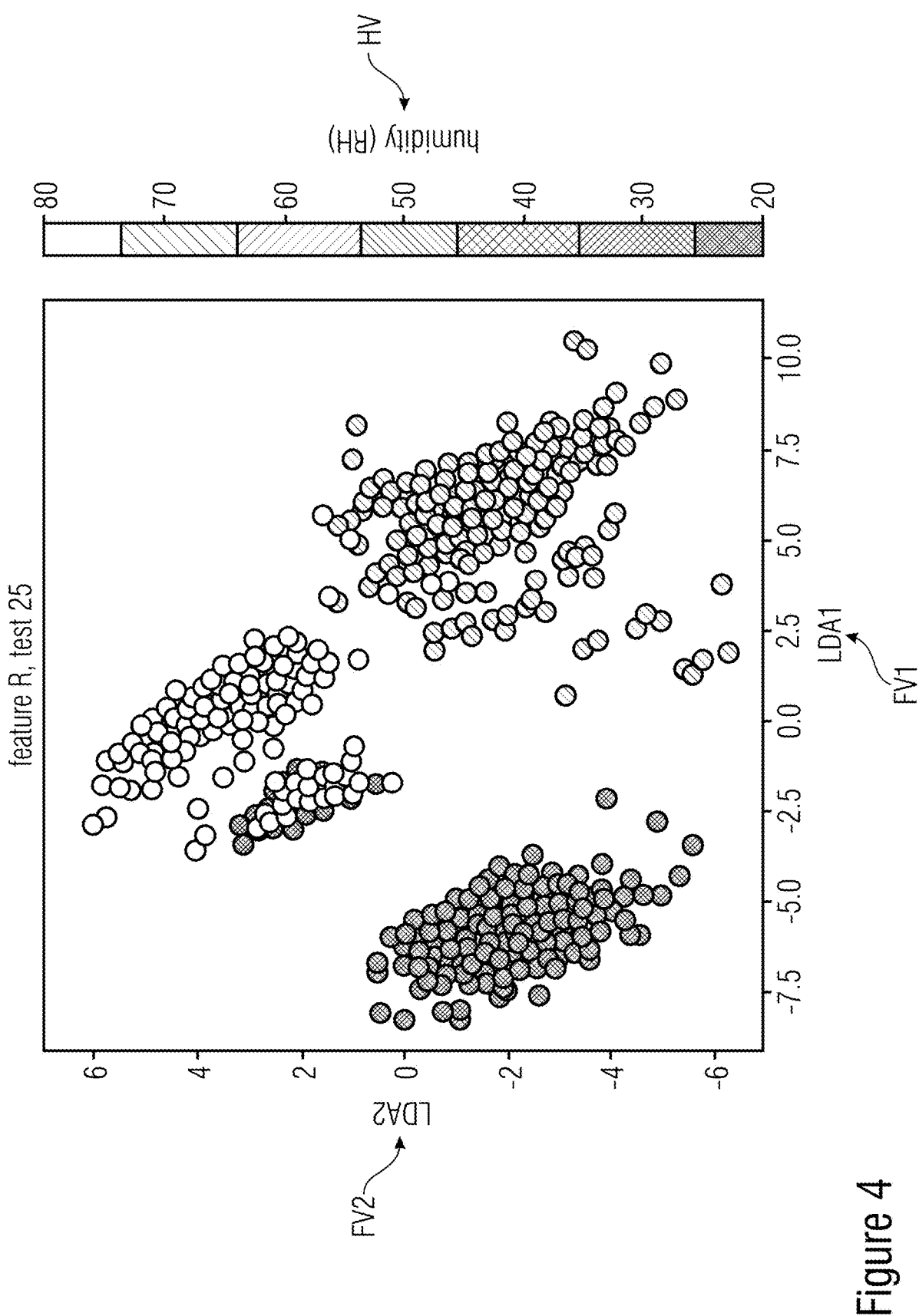
FIG. 4 shows an exemplary two-dimensional representation of the most informative feature values extracted from the signal samples and the assignment of the most informative feature values to humidity values.

FIG. 4 shows an exemplary two-dimensional representation of the most informative feature values FV1, FV2 extracted from the signal samples SIG and the assignment of the most informative feature values FV1, FV2 to humidity values HV.

In particular, FIG. 4 shows how a parametric classifier can easily separate and cluster various humidity values out of two features obtained from the sensor raw data.

The choice between a parametric classifier and a non-parametric NN based regression depends on the level of granularity desired for the additional humidity output to be provided to the user.

Figure 5:
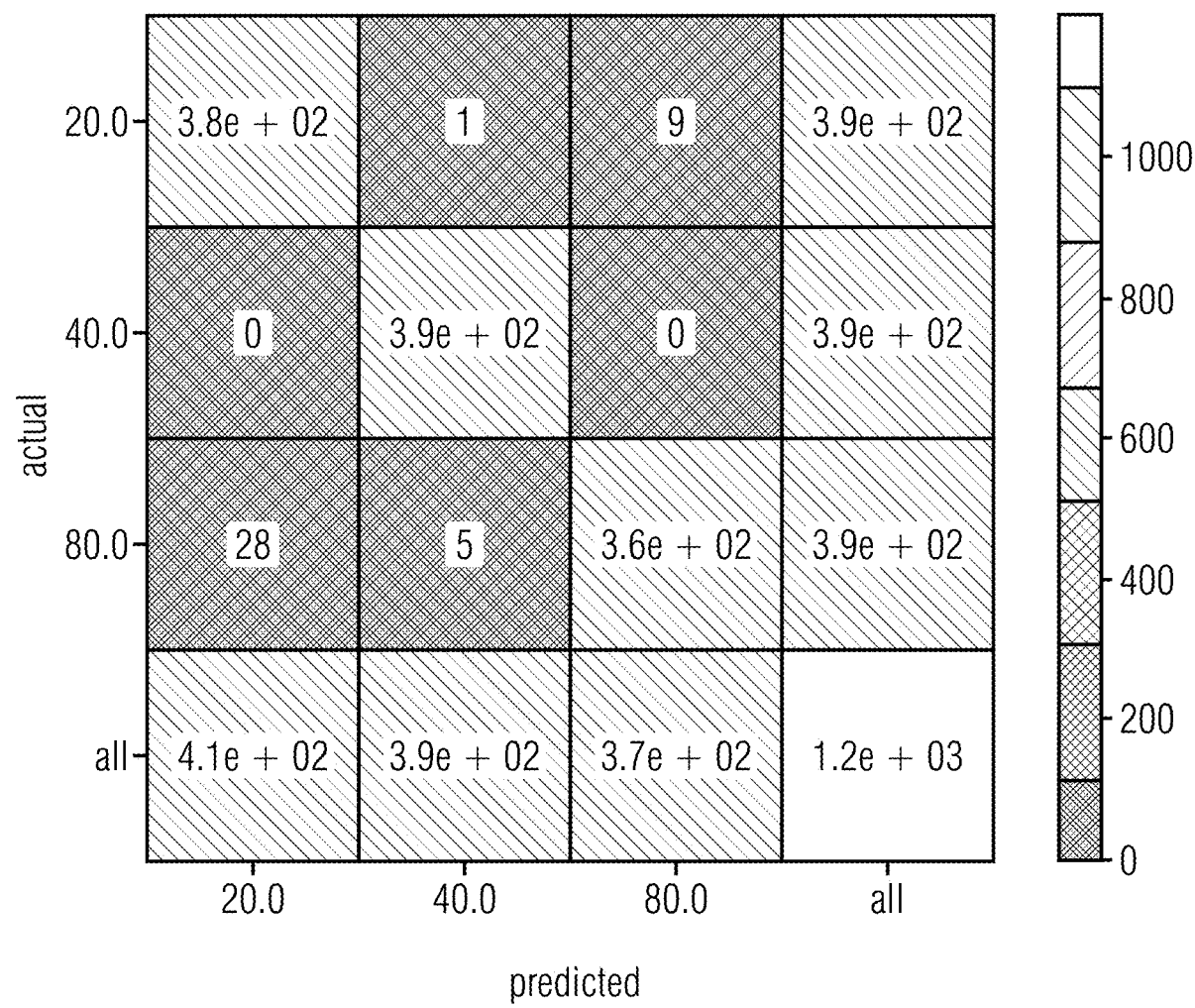
FIG. 5 shows an exemplary confusion matrix visualizing the performance of a humidity processor according to the disclosure.

FIG. 5 shows an exemplary confusion matrix visualizing the performance of a humidity processor 6 according to the disclosure.

In particular, FIG. 5 shows the confusion matrix for a humidity classification based on a shallow neural network having one hidden layer and eight nodes. From the 1200 classifications only 43 have been proven as being wrong.

At this point, the predicted humidity values can be sent to the gas concentration processor 11, which is estimating the gas concentrations, and which typically comprises a fully connected neural network or a gated recurrent unit. It can be seen in FIG. 3 that the predicted humidity values HV come as an additional feature to the neural network 12 and thus replace a humidity sensor and can be even separately displayed in the graphical user interface 16 if desired.

Figure 6:
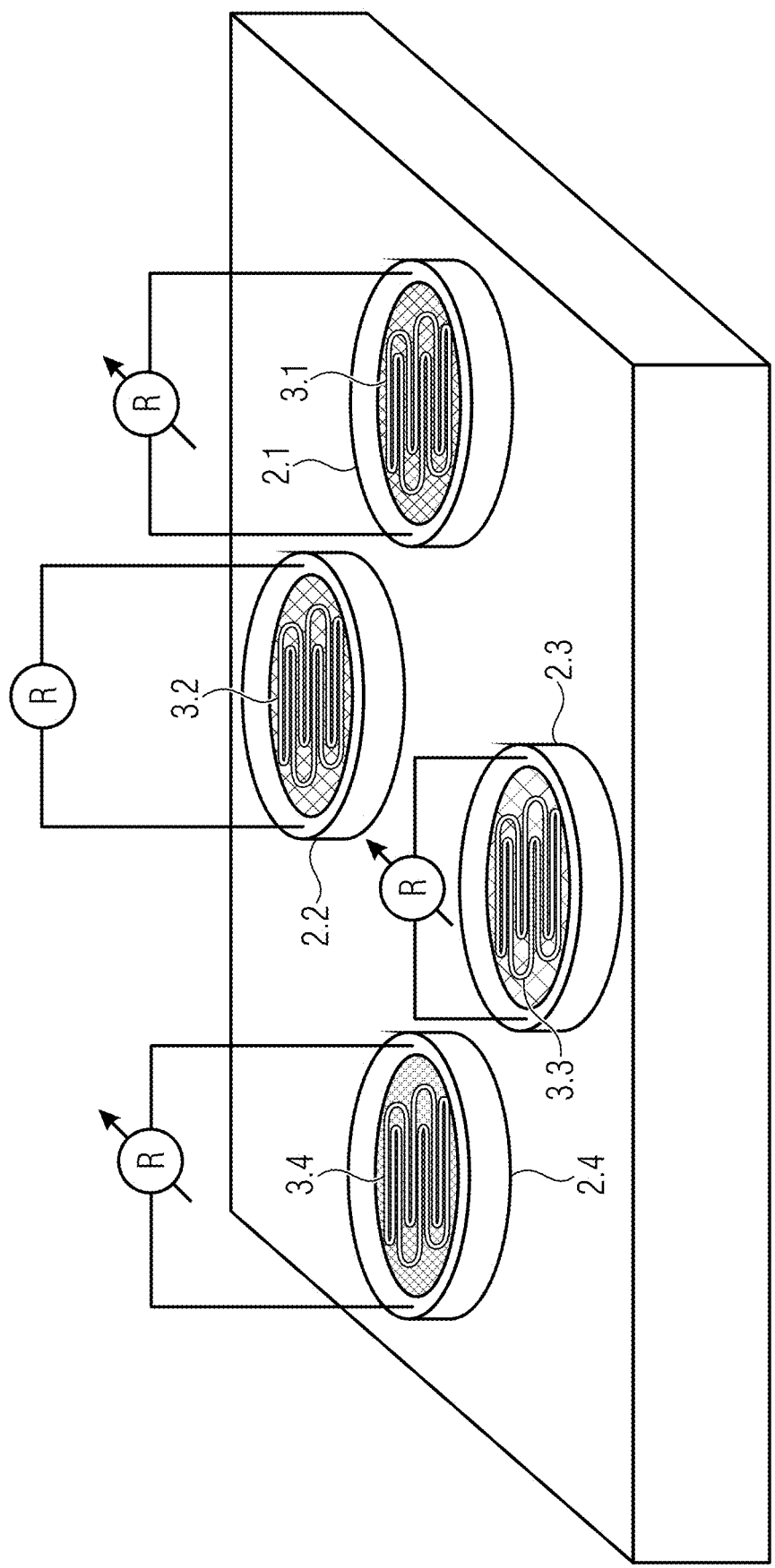
FIG. 6 shows an exemplary graphene multi-gas sensor array according to the disclosure.

FIG. 6 shows an exemplary graphene multi-gas sensor array 2 according to the disclosure. Each sensor 2.1, 2.2, 2.3 and 2.4 in the array has a heat source 3.1, 3.2, 3.3, 3.4 whose temperature is being pulsed between first temperature (T1, recovery phase) and a second temperature (T2, sense phase). The result of these controlled temperature oscillations is a more dynamic behavior of the signal samples SIG1, SIG2, SIG3, SIG4 as shown in FIG. 7 which is exploited by the gas sensing device 1.

Several implementations of temperature pulsing mechanism are possible. For example, the temperature modulation could be the same for all sensors 2.1, 2.2, 2.3 and 2.4 or different in order to better exploit the different functionalizations of the base material and to improve gas separability. Similarly, multiple heater controls can be used (one for each sensor 2.1, 2.2, 2.3 and 2.4) or, alternatively, a single heater control in time division multiplexing with different applied voltages so as to obtain sensor specific temperature values.

The sensors 2.1, 2.2, 2.3 and 2.4 form a multi-gas sensor array, where a base material consisting of graphene is functionalized with different chemicals (e.g. Pd, Pt, and $MnO_2$) for dissimilar selectivity. The interaction between graphene sheets and absorbed gas analytes would influence the electronic structure of the material, resulting in altered charge carrier concentrations and changed electrical conductance. Meanwhile, due to different sensitivity towards various gas molecules resistances of the sensors 2.1, 2.2, 2.3 and 2.4 also change in disparate patterns, making it possible to analyze complicated gas mixtures with one single sensor array.

Figure 7:
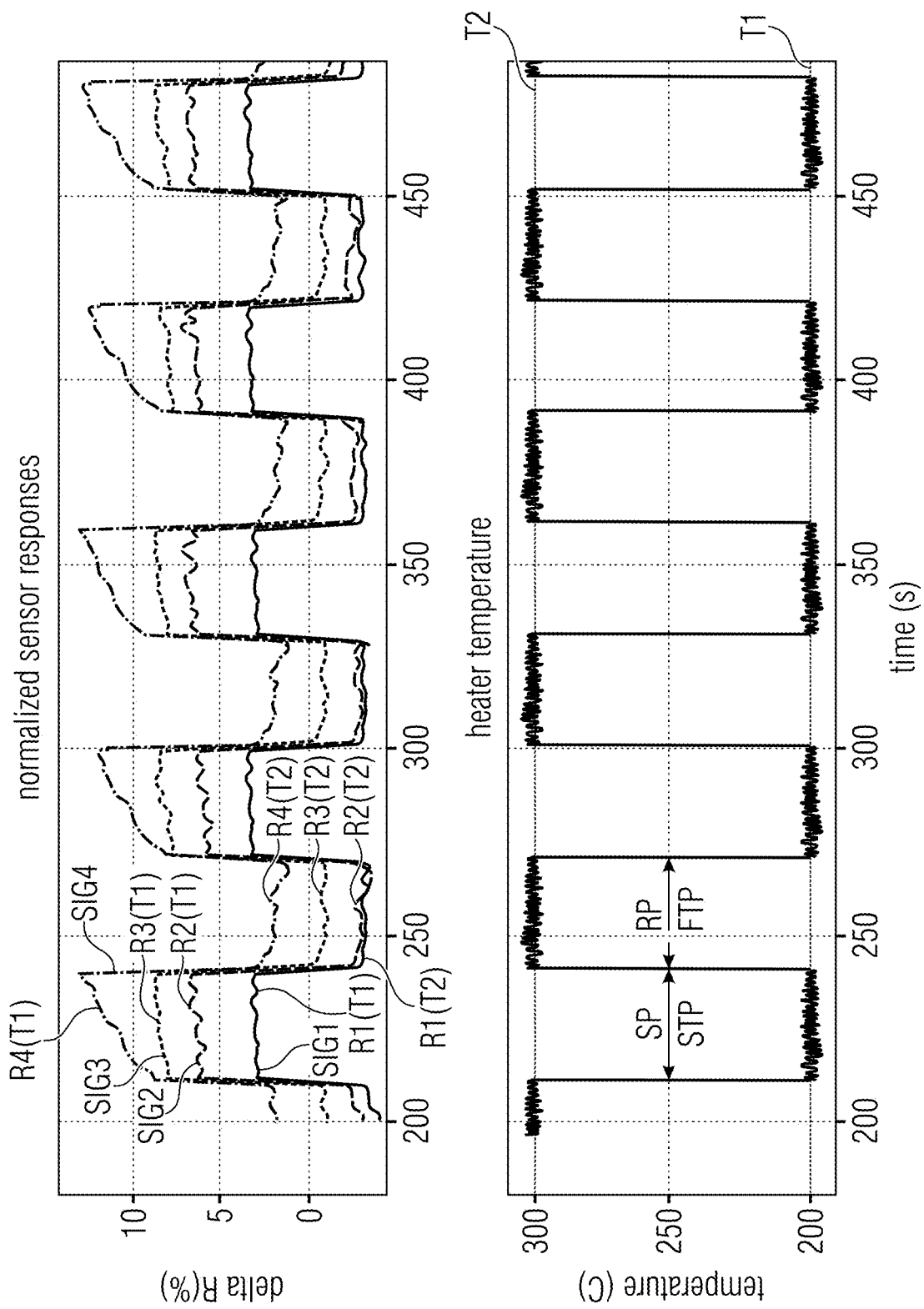
FIG. 7 illustrates exemplary normalized sensor responses and heater temperatures over time.

FIG. 7 illustrates exemplary normalized signal samples SIG1, SIG2, SIG3 SIG4 for the chemo-resistive gas sensors 2.1, 2.2, 2.3, 2.4 and temperature profiles FTP, STP over time. In the particular example of FIG. 7 two temperatures profiles FTP, STP are chosen: A first temperature profile FTP for sensing the sensor resistances and for recovering the sensors surface and desorb adsorbed gas molecules at a constant temperature of 300° C. in a recovery phase RP and a second temperature profile STP for sensing the sensor resistances at a constant temperature of 200° C. during a sense phase SP. Therefore, not only static features like absolute or relative sensor resistance changes can be monitored, but also dynamic features like e.g. the slope of the sense phase SP at 200° C. which reflects the gas adsorption over time. Additional temperature steps and pulse modes are also possible, as long as they contribute additional information or features to the signal samples SIG1, SIG2, SIG3 and SIG4 like gas adsorption/reaction at a certain temperature or temperature ramp.

Figure 8:
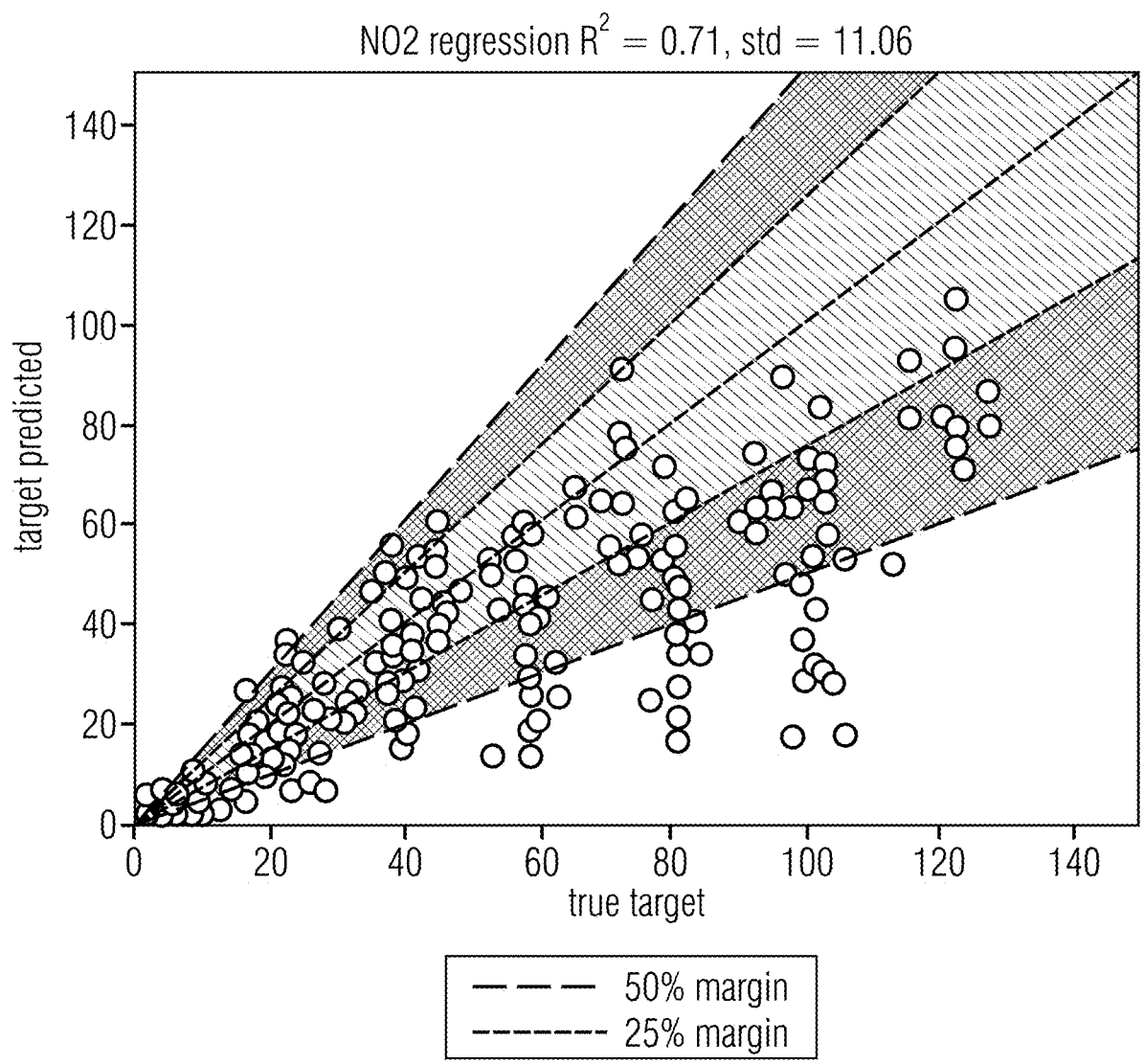
FIG. 8 shows exemplary results for sensing of $N_{OX}$ using a chemo-resistive gas sensing device having a distinguished humidity sensor according to prior art.

FIG. 8 shows exemplary results for sensing of NOX using a chemo-resistive gas sensing device having a distinguished humidity sensor according to prior art.

Figure 9:
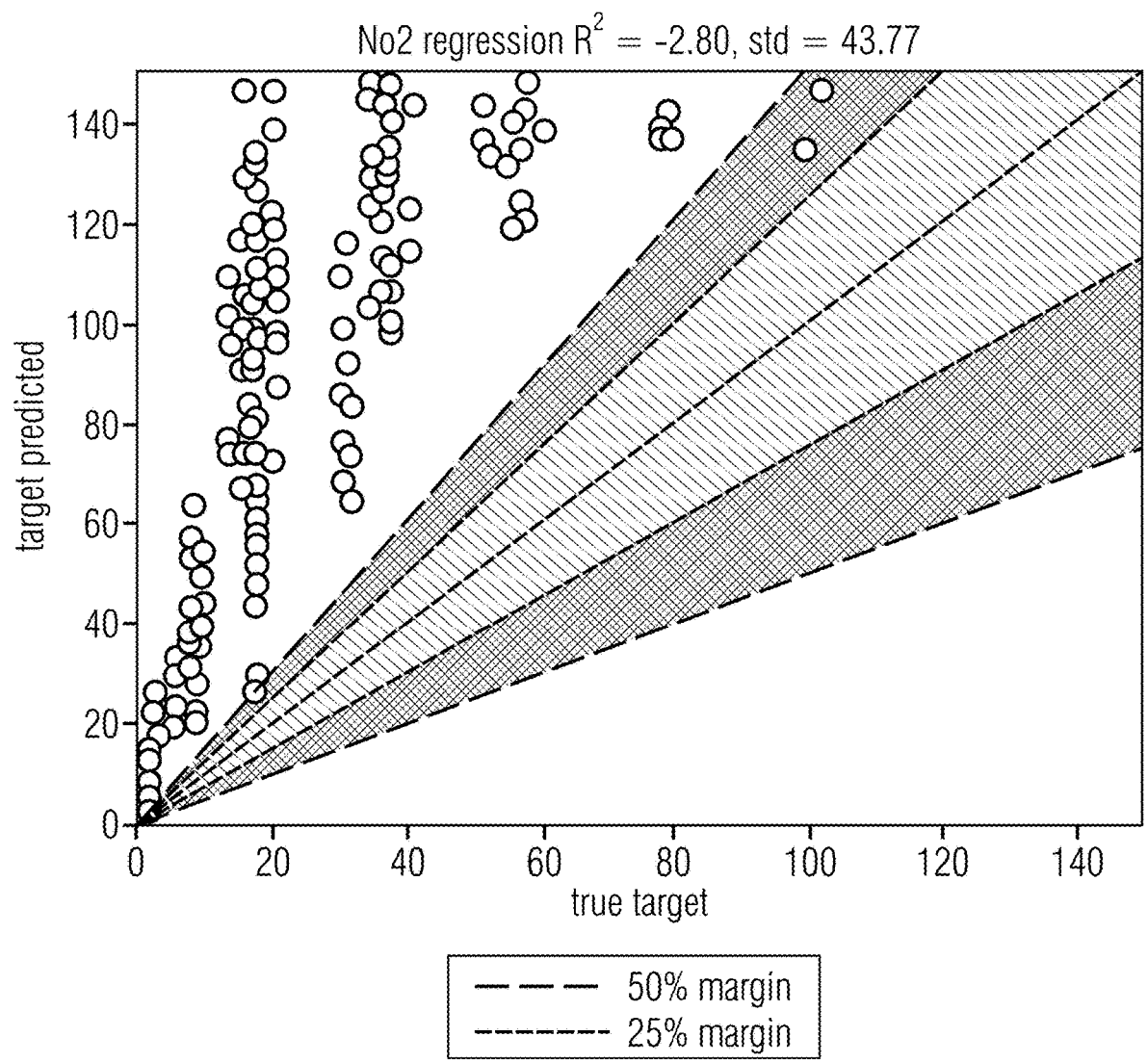
FIG. 9 shows exemplary results for sensing of $N_{OX}$ using a chemo-resistive gas sensing device without humidity compensation according to prior art.

FIG. 9 shows exemplary results for sensing of NOX using a chemo-resistive gas sensing device without humidity compensation according to prior art.

Figure 10:
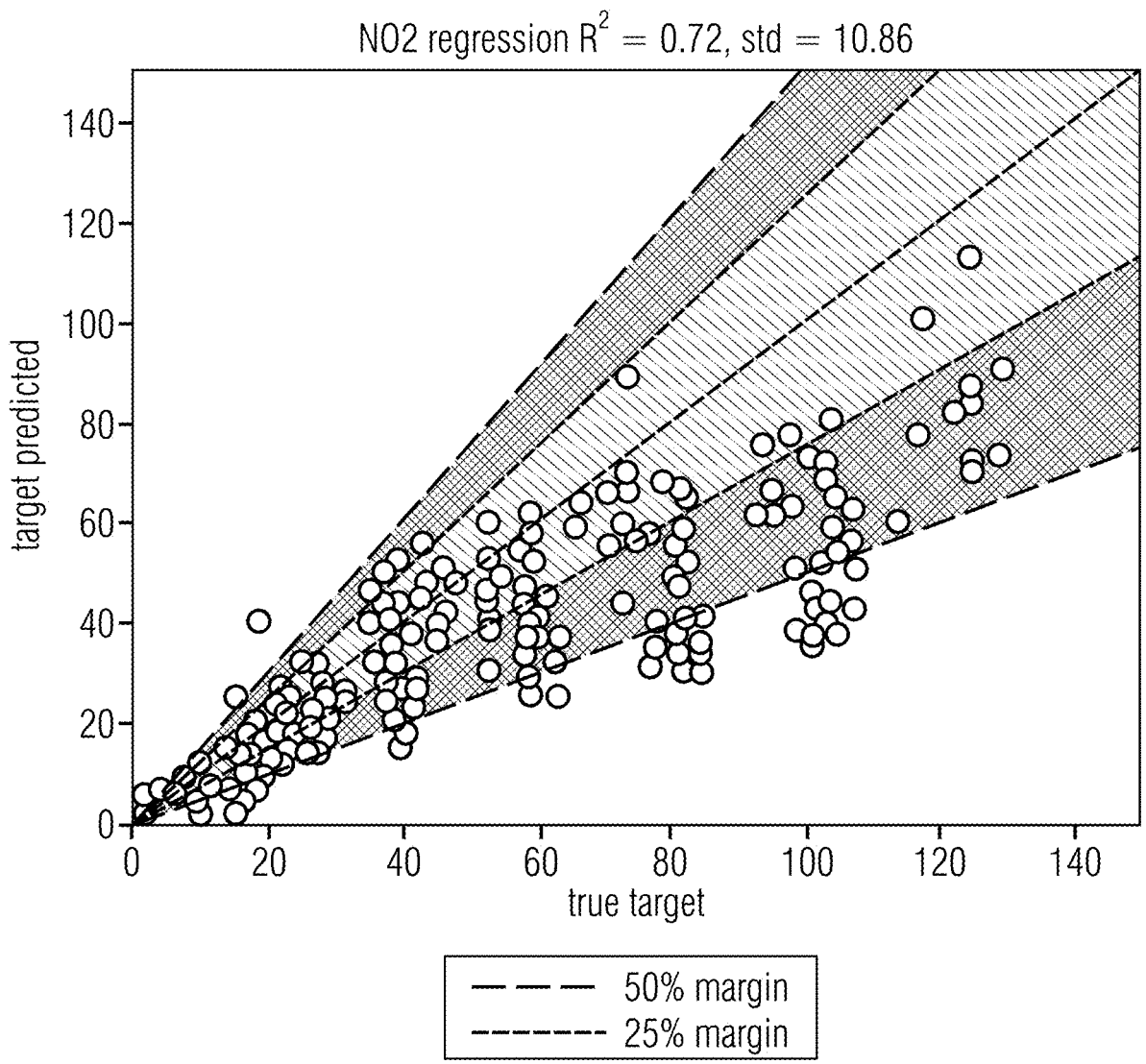
FIG. 10 shows exemplary results for sensing of $N_{OX}$ using a chemo-resistive gas sensing device having a humidity processor according to the disclosure.

FIG. 10 shows exemplary results for sensing of NOX using a chemo-resistive gas sensing device 1 having a humidity processor 6 according to the disclosure.

In FIGS. 8 to 10 preliminary results obtained by adopting the proposed scheme on some of the data collected in a lab for different humidity values are shown. Here the target gas of interest is NO2 for outdoor air quality monitoring applications. Specifically, the ideal case where humidity is perfectly know (FIG. 8) is compared to the case where a fixed humidity value is used to prepare the gas estimation model (FIG. 9) and to the solution proposed in this disclosure (FIG. 10) where humidity is estimated and passed to the gas prediction model. The humidity knowledge in FIG. 8 can be either obtained by a reference humidity sensor or knowing the set humidity condition. In FIG. 9 the fixed humidity value refers to training/calibrating the sensor at a single humidity value (e.g Rh 45%, Rt 25 C) and using the generated model for all relative humidity conditions.

Figure 11:
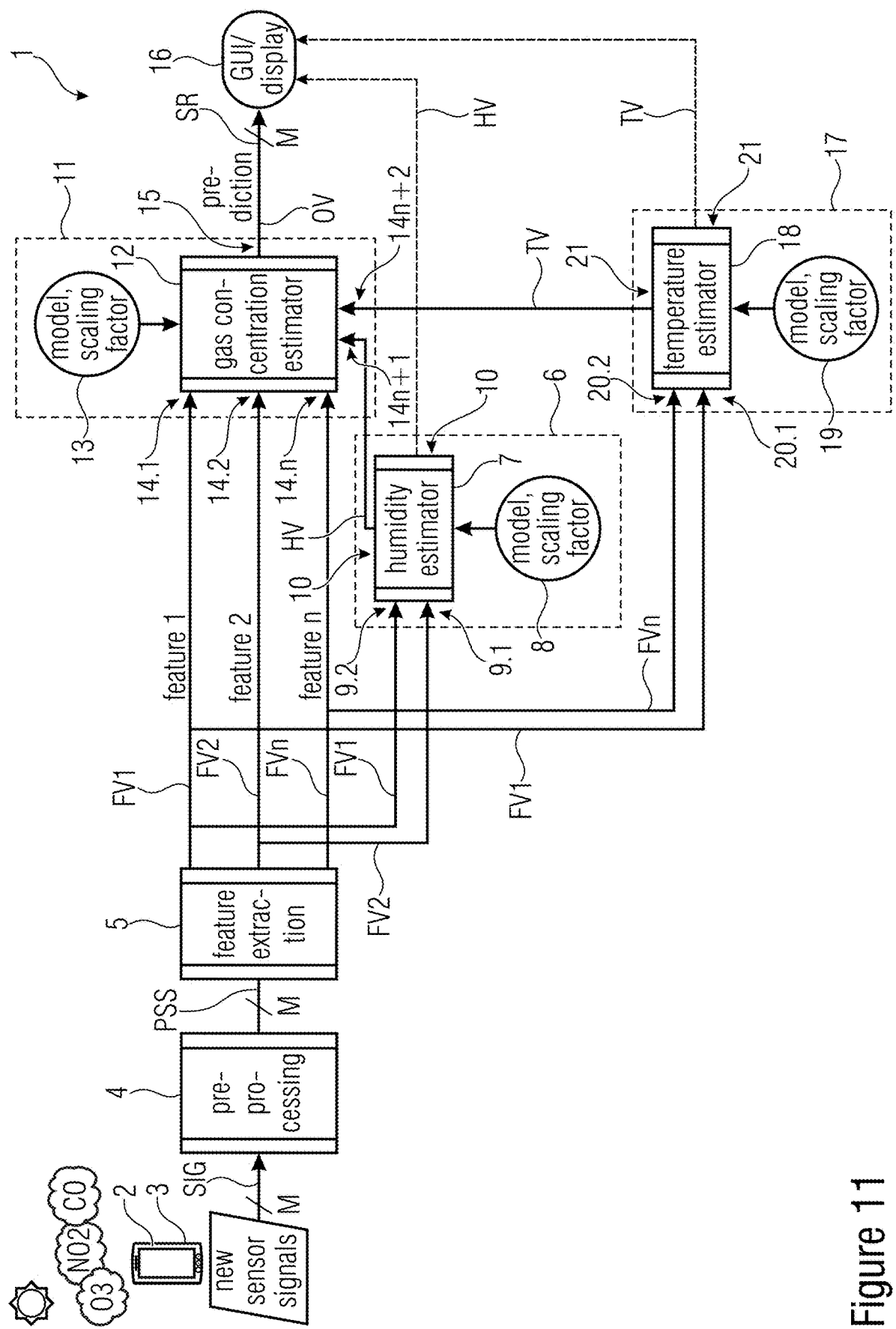
FIG. 11 shows a schematic view of a third exemplary embodiment of a gas sensing device according to the disclosure.

FIG. 11 shows a schematic view of a third exemplary embodiment of a gas sensing device 1 according to the disclosure.

According to embodiments of the disclosure the gas sensing device 1 comprises a temperature processor 17 configured for receiving a third group of the feature values FV and for estimating a temperature value TV of the mixture of gases, wherein the temperature processor 17 comprises a third trained model based algorithm processor 18 and a third trained model 19 for the third trained model based algorithm processor 18, wherein the third group of feature values FV is fed to inputs 20 of the third trained model based algorithm processor 18, and wherein the temperature value TV is based on an output 21 of the third machine learning algorithm processor 18;

wherein the gas concentration processor 11 is configured for receiving the temperature value TV, and wherein the sensing results SR are based on the temperature value TV.

According to embodiments of the disclosure the third trained model based algorithm processor 18 is implemented as a third artificial neural network.

According to embodiments of the disclosure the temperature value TV is fed to one of the inputs 14 of the second trained model based algorithm processor 12 in order to make the sensing results SR dependent on the temperature value TV.

According to embodiments of the disclosure the gas sensing device 1 comprises an output unit 16 configured for outputting the temperature value TV.

Figure 12:
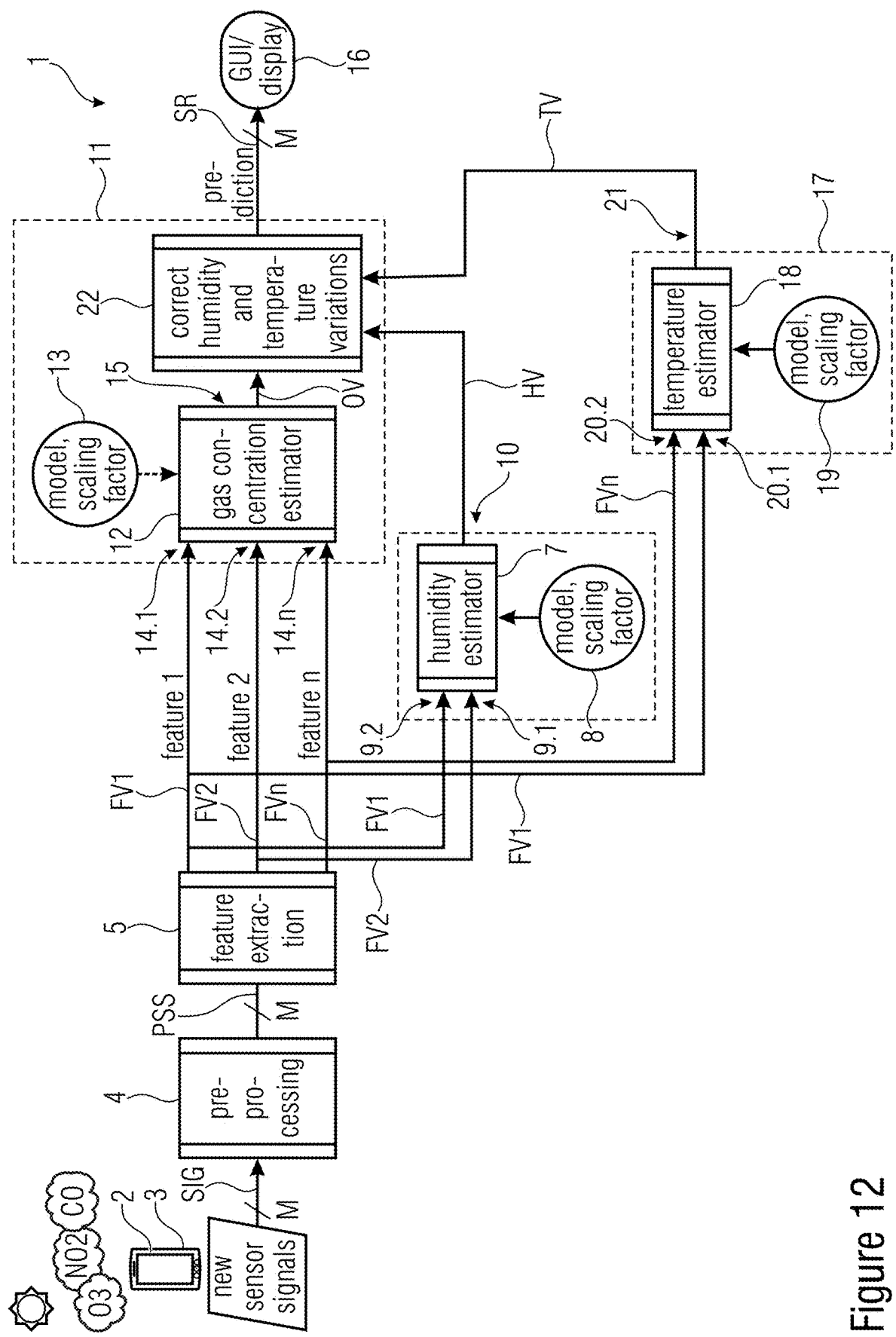
FIG. 12 shows a schematic view of a fourth exemplary embodiment of a gas sensing device according to the disclosure.

FIG. 12 shows a schematic view of a fourth exemplary embodiment of a gas sensing device 1 according to the disclosure.

According to embodiments of the disclosure the gas concentration processor 11 comprises a correction processor 22 for correcting the output values OV of the second machine learning algorithm processor 12, wherein the humidity value HV is fed to the correction processor 22, wherein the correction processor 22 is configured for correcting the output values OV of the second machine learning algorithm processor 12 depending on the humidity value HV in order to make the sensing results SR dependent on the humidity value HV.

According to embodiments of the disclosure the gas concentration processor 11 comprises a correction processor 22 for correcting the output values OV of the second machine learning algorithm processor 12, wherein the temperature value TV is fed to the correction processor 22, wherein the correction processor 22 is configured for correcting the output values OV of the second machine learning algorithm processor 12 depending on the temperature value TV in order to make the sensing results SR dependent on the temperature value TV.

According to embodiments of the disclosure the correction processor 22 comprises on or more lookup tables for correcting the output values OV of the second machine learning algorithm processor 12.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:
1. A gas sensing device for sensing one or more gases in a mixture of gases; the gas sensing device comprising:
one or more chemo-resistive gas sensors, wherein each of the gas sensors is configured for generating signal samples corresponding to a concentration of one of the one or more gases in the mixture of gases, wherein the one or more gas sensors are alternately operated in recovery phases and in sense phases, wherein at least some of the signal samples of each of the gas sensors represent one of the recovery phases and one of the sense phases;
one or more heat sources for heating the gas sensors according to one or more first temperature profiles during the recovery phases and according to one or more second temperature profiles during the sense phases wherein for each of the gas sensors a maximum temperature of the respective first temperature profile is higher than a maximum temperature of the respective second temperature profile;
preprocessing processor configured for receiving the signal samples from each of the gas sensors and for preprocessing the received signal samples in order to generate preprocessed signal samples for each of the gas sensors;
feature extraction processor configured for receiving the preprocessed signal samples and for extracting one or more feature values from the received preprocessed signal samples of each of the gas sensors based on characteristics of the received preprocessed signal samples of the respective gas sensor;
a humidity processor configured for receiving a first group of the feature values and for estimating a humidity value of the mixture of gases, wherein the humidity processor comprises a first trained model based algorithm processor and a first trained model for the first trained model based algorithm processor, wherein the first group of feature values is fed to inputs of the first trained model based algorithm processor, and wherein the humidity value is based on an output of the first machine learning algorithm processor; and a gas concentration processor configured for receiving a second group of the feature values and the humidity value, and creating for each of the gas sensors sensing results, wherein the gas concentration processor comprises a second trained model based algorithm processor and a second trained model for the second trained model based algorithm processor wherein the second group of feature values is fed to inputs of the second trained model based algorithm processor, wherein the sensing results are based on output values at one or more outputs of the second machine learning algorithm processor, and wherein the sensing results depend on the humidity value.

2. A gas sensing device according to claim 1, wherein the preprocessing processor is configured for executing a baseline calibration algorithm for the signal samples received from the gas sensors.

3. A gas sensing device according to claim 1, wherein the preprocessing processor is configured for executing a filtering algorithm for the signal samples received from the gas sensors.

4. A gas sensing device according to claim 1, wherein the preprocessing processor is configured for executing a sense phase extraction algorithm for the signal samples received from the gas sensors.

5. A gas sensing device according to claim 1, wherein the feature extraction processor is configured for extracting from the received preprocessed signal samples a normalized sensor sensitivity as one of the feature values for each of the gas sensors.

6. A gas sensing device according to claim 1, wherein the feature extraction processor is configured for extracting from the received preprocessed signal samples a slope of one of the preprocessed signal samples as one of the feature values for each of the gas sensors.

7. A gas sensing device according to claim 1, wherein the feature extraction processor is configured for extracting from the preprocessed signal samples received from the gas sensors a ratio between an average value of one of the preprocessed signal samples during the sense phase of the one of the preprocessed signal samples and an average value of the one of the preprocessed signal samples during the recovery phase of the one of the preprocessed signal samples as one of the feature values for each of the gas sensors.

8. A gas sensing device according to claim 1, wherein the feature extraction processor is configured for extracting from the preprocessed signal samples received from the gas sensors a difference between an average value of one of the preprocessed signal samples during the sense phase of the one of the preprocessed signal samples and an average value of the one of the preprocessed signal samples during the recovery phase of the one of the preprocessed signal samples as one of the feature values for each of the gas sensors.

9. A gas sensing device according to claim 1, wherein the first trained model based algorithm processor is implemented as a first artificial neural network.

10. A gas sensing device according to claim 1, wherein the second trained model based algorithm processor is implemented as a second artificial neural network.

11. A gas sensing device according to claim 1, wherein the humidity value is fed to one of the inputs of the second trained model based algorithm processor in order to make the sensing results dependent on the humidity value.

12. A gas sensing device according to claim 1, wherein the gas sensing device comprises a temperature processor configured for receiving a third group of the feature values and for estimating a temperature value of the mixture of gases, wherein the temperature processor comprises a third trained model based algorithm processor and a third trained model for the third trained model based algorithm processor, wherein the third group of feature values is fed to inputs of the third trained model based algorithm processor, and wherein the temperature value is based on an output of the third machine learning algorithm processor, and
wherein the gas concentration processor is configured for receiving the temperature value, and wherein the sensing results are based on the temperature value.

13. A gas sensing device according to claim 12, wherein the third trained model based algorithm processor is implemented as a third artificial neural network.

14. A gas sensing device according to claim 12, wherein the temperature value is fed to one of the inputs of the second trained model based algorithm processor in order to make the sensing results dependent on the temperature value.

15. A gas sensing device according to claim 1, wherein the gas concentration processor comprises a correction processor for correcting the output values of the second machine learning algorithm processor, wherein the humidity value is fed to the correction processor, wherein the correction processor is configured for correcting the output values of the second machine learning algorithm processor depending on the humidity value in order to make the sensing results dependent on the humidity value.

16. A gas sensing device according to claim 12, wherein the gas concentration processor comprises a correction processor for correcting the output values of the second machine learning algorithm processor, wherein the temperature value is fed to the correction processor, wherein the correction processor is configured for correcting the output values of the second machine learning algorithm processor depending on the temperature value in order to make the sensing results dependent on the temperature value.

17. A gas sensing device according to claim 15, wherein the correction processor comprises on or more lookup tables for correcting the output values of the second machine learning algorithm processor.

18. A gas sensing device according to claim 1, wherein the gas sensing device comprises an output unit configured for outputting the sensing results and/or the humidity value.

19. A gas sensing device according claim 12, wherein the gas sensing device comprises an output unit configured for outputting the temperature value.

20. A method for operating a gas sensing device for sensing one or more gases in a mixture of gases; the gas sensing device comprising one or more chemo-resistive gas sensors, wherein the method comprises:
using each of the gas sensors for generating signal samples corresponding to a concentration of one of the one or more gases in the mixture of gases, wherein the one or more gas sensors are alternately operated in recovery phases and in sense phases, wherein at least some of the signal samples of each of the gas sensors represent one of the recovery phases and one of the sense phases;
using one or more heat sources for heating the gas sensors according to one or more first temperature profiles during the recovery phases and according to one or more second temperature profiles during the sense phases, wherein for each of the gas sensors a maximum temperature of the respective first temperature profile is higher than a maximum temperature of the respective second temperature profile;

using a preprocessing processor for receiving the signal samples from each of the gas sensors and for preprocessing the received signal samples in order to generate preprocessed signal samples for each of the gas sensors;

using a feature extraction processor for receiving the preprocessed signal samples and for extracting one or more feature values from the received preprocessed signal samples of each of the gas sensors based on characteristics of the received preprocessed signal samples of the respective gas sensor;

using a humidity processor for receiving a first group of the feature values and for estimating a humidity value of the mixture of gases, wherein the humidity processor comprises a first trained model based algorithm processor and a first trained model for the first trained model based algorithm processor, wherein the first group of feature values is fed to inputs of the first trained model based algorithm processor, and wherein the humidity value is based on an output of the first machine learning algorithm processor; and using a gas concentration processor for receiving a second group of the feature values and the humidity value, and creating for each of the gas sensors sensing results, wherein the gas concentration processor comprises a second trained model based algorithm processor and a second trained model for the second trained model based algorithm processor, wherein the second group of feature values is fed to inputs of the second trained model based algorithm processor, wherein the sensing results are based on output values at one or more outputs of the second machine learning algorithm processor, and wherein the sensing results depend on the humidity value.

* * * * *